United States Patent

Devanathan et al.

Patent Number: 5,645,594
Date of Patent: Jul. 8, 1997

[54] POLYMER COMPOSITE IMPLANT AND METHOD OF MAKING THE SAME

[75] Inventors: Thirumalai Devanathan; Richard S. King, both of Warsaw, Ind.

[73] Assignee: Zimmer, Inc., Warsaw, Ind.

[21] Appl. No.: 557,246

[22] Filed: Nov. 14, 1995

Related U.S. Application Data

[63] Continuation of Ser. No. 225,873, Apr. 11, 1994, abandoned.

[51] Int. Cl.$^6$ .................................................. A61F 2/28
[52] U.S. Cl. ........................ 623/16; 623/22; 433/180; 433/226
[58] Field of Search .................... 623/16, 18, 22, 623/23; 433/228.1, 226, 201.1, 180

[56] References Cited

U.S. PATENT DOCUMENTS

| | | | |
|---|---|---|---|
| 4,266,303 | 5/1981 | Park | 3/1.91 |
| 4,336,618 | 6/1982 | Raab | 623/16 |
| 4,432,730 | 2/1984 | Gettleman et al. | 433/168 |
| 4,566,138 | 1/1986 | Lewis et al. | 623/22 |
| 4,735,625 | 4/1988 | Davidson | 623/16 |
| 5,260,093 | 11/1993 | Kamel et al. | 427/2 |
| 5,314,494 | 5/1994 | Huiskes et al. | 623/23 |

FOREIGN PATENT DOCUMENTS

| | | |
|---|---|---|
| 0 120 595 | 10/1984 | European Pat. Off. . |
| 0 529 264 A2 | 3/1993 | European Pat. Off. . |
| 38 38 568 A1 | 5/1990 | Germany . |
| 2 045 082 | 10/1980 | United Kingdom . |
| WO 86/02260 | 4/1986 | WIPO . |

Primary Examiner—John G. Weiss
Assistant Examiner—Bruce Snow
Attorney, Agent, or Firm—Todd A. Dawson

[57] ABSTRACT

This invention provides for an acetabular cup and the manufacturing of an acetabular cup implant formed from a composite of polymer materials such that the articulating surface of the implant is 100% ultra high molecular weight poly ethylene (UHMWPE) and the bone engaging surface of the cup contains a significant amount of poly methyl methacrylate (PMMA). The cup would consist of at least two zones. Zone 1 forming the articulating surface and zone two extending from the zone 1 to the bone engaging surface. Preferably, the zone 1 would consist of UHMWPE and would extend a predetermined thickness from the articulating surface. Zone 2 would preferably consist of a mixture of UHMWPE and PMMA dry blended before molding. A third zone may abut zone 2 and consist of PMMA.

5 Claims, 1 Drawing Sheet

POLYMER COMPOSITE IMPLANT AND METHOD OF MAKING THE SAME

This application is a continuation of application Ser. No. 08/225,873 filed Apr. 11, 1994, now abandoned.

FIELD OF THE INVENTION

This invention relates to implants made from a polymer material and has specific relevance to an implant having an articulating surface made from one form of the polymer and a substantial portion formed from a composite material.

BACKGROUND OF THE INVENTION

Prosthetic acetabular cups as used in total hip replacement surgery have been made from a variety of materials throughout the years. Cups have been made from all metals, from all polymers or from a combination of materials wherein the outer shell is formed from metal and the liner which forms the articulating surface is formed from a polymer. The choice of polymer varies from manufacturer to manufacturer, but ultra high molecular weight polyethylene (UHMWPE) is widely used.

Prosthetic cups are made to be screwed to the acetabulum, are press fitted to the acetabulum, or may be cemented to the acetabulum depending on the surgeon's preference for the particular patient. Several advantages and disadvantages are associated with each style of cup as well as its particular fixation method. One disadvantage to an all UHMWPE cup is that cement fixation is difficult as bone cement does not adhere well to UHMWPE. Further, an all UHMWPE cup exhibits creep problems when implanted into the body as the glass transition temperature of UHMWPE is lower than the temperature of a patient's body.

SUMMARY OF THE INVENTION

This invention provides for an acetabular cup and the manufacturing of an acetabular cup implant formed from a composite of polymer materials such that the articulating surface of the implant is 100% ultra high molecular weight poly ethylene (UHMWPE) and the bone engaging surface of the cup is essentially poly methyl methacrylate (PMMA). The cup would consist of at least two zones. Zone 1 forming the articulating surface and zone two extending from the zone 1 to the bone engaging surface. Preferably, the zone 1 would consist of UHMWPE and would extend a predetermined thickness from the articulating surface. Zone 2 would preferably consist of a mixture of UHMWPE and PMMA dry blended before molding. A third zone would consist essentially of PMMA.

Accordingly, it is an object of this invention to provide for a novel polymer composite implant.

Another object of the invention is to provide for an prosthetic acetabular cup having a substantial portion of the cup formed from a mixture of PMMA and UHMWPE.

Another object of the invention is to provide for an acetabular cup having a layer of UHMWPE forming an articulating surface and a body formed from a mixture of PMMA and UHMWPE.

Another object of the invention is to provide a novel method of forming a composite polymer implant.

Other objects of the invention will become apparent upon a reading of the following description taken with the accompanying drawings.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

Figure 1:
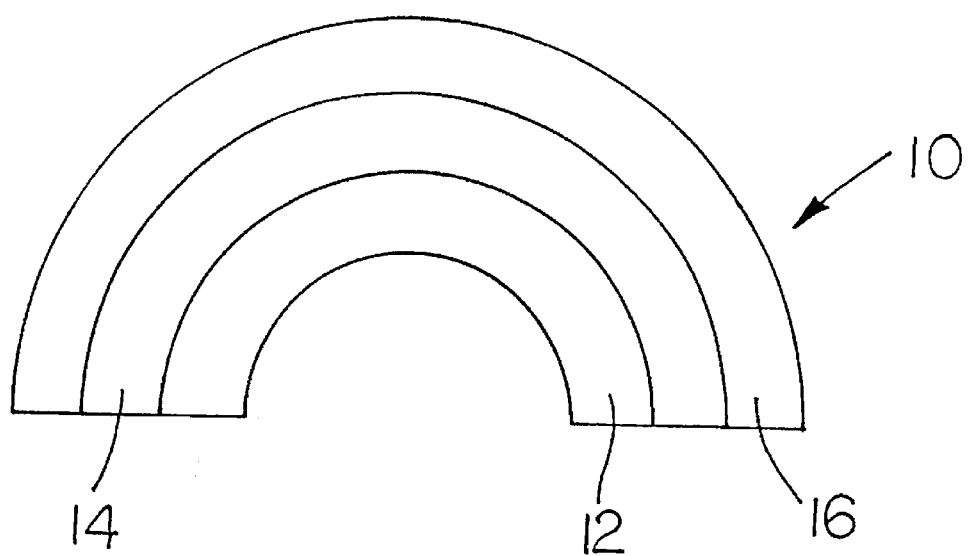
FIG. 1 is a cross-sectional view of a prosthetic acetabular cup illustrating the invention.

The acetabular cup 10 of the invention as illustrated in cross section FIG. 1 includes three layers or zones. Zone I or layer 12 is formed from a polymer material from the polyethylene family and most preferably ultra high molecular weight polyethylene (UHMWPE) which forms an articulating surface for accommodating the femoral head of a hip stem implant (not shown). UHMWPE is well known in the orthopaedic industry. Zone 2 or layer 14 of cup 10 is formed from a polymer blend of UHMWPE and PMMA. Either PMMA homopolymers or PMMA copolymers may be used. The polymer blend forms an inter-penetrating polymer network which provides high integrity under loading conditions. Zone 3 or layer 16 consists of 100% PMMA, either PMMA homopolymer or PMMA copolymer. A spacer formed from PMMA may be affixed by ultrasonic welding to layer 13 as illustrated in FIG. 1 to assist the surgeon in providing a uniform cement mantle about the cup when implanted. To form the implant of FIG. 1, a layer of PMMA particles or formed PMMA film is placed within the female part of a compression mold. Next, a layer of PMMA and UHMWPE particles which have been dry blended is placed within the mold over the PMMA layer. Preferably, the blend includes 20% to 30% of PMMA by weight. It may be necessary to pre-consolidate the layers prior to adding the next adjacent layer by applying pressure to the layers after the particles are placed into the mold. Finally, a layer of UHMWPE particles is placed over the layer of blended PMMA & UHMWPE particles. The mold is closed and compression molded under pressure and temperature. During molding, the PMMA melts and forms an inter-penetrating thermoplastic network in the UHMWPE which allows for an increased stiffness in the cup as compared to all UHMWPE cups. Further, the cup of the invention provides reduced compression creep as compared to all UHMWPE cups as the glass transition temperature of PMMA is higher than that of the UHMWPE and of the patient's body. Finally, by forming Zone 3 or layer 16 from PMMA, the cup would readily bond to the PMMA bone cement placed in the acetabulum to cement the cup in place.

Figure 2:
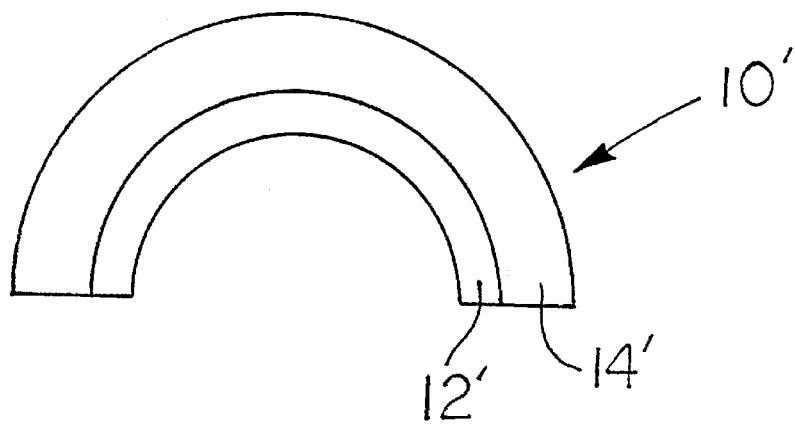
FIG. 2 is an alternative embodiment of the invention.

An alternative embodiment of the invention is illustrated in FIG. 2. The cup 10' of FIG. 2 includes a layer 12' of UHMWPE and a layer 14' of blended UHMWPE and PMMA. The manner of making cup 10' is similar to that described above except that the step of applying a layer of PMMA as Zone 3 is eliminated. In use, after the surgeon prepares the patient's acetabulum and applies a PMMA bone cement therein, the implant 10' is seated in the bone cement. The fresh bone cement placed within the acetabulum interacts with the bone cement in layer 14' to bond the implant in place.

It should be understood that while the invention is described as relating to an acetabular component, the method would have application to a variety of implants such as a tibial tray. Modification of the method for use with a different implant component would be considered within the scope of the invention.

It should be also understood that while specific thickness for the zones have not been discussed, the thickness of each zone or layer could be controlled to vary the stiffness of the implant depending upon the manufactures specifications.

Further, it should be understood that the invention is not limited to the precise forms disclosed but may be modified within the scope of the appended claims.

We claim:

1. A non-metallic orthopaedic implant comprising:

a first layer adapted for sliding contact with a second component, a second outer layer, the first layer being formed from a polymer material from a family of polyethylene, the second layer being formed from a homogeneous blend of polyethylene and poly methyl methacrylate.

2. The non-metallic implant of claim 1 wherein the first layer is formed from ultra high molecular weight polyethylene.

3. The non-metallic implant of claim 1 further including a third layer molded to the second outer layer, the third layer consisting of poly methyl methacrylate.

4. The implant of claim 1 including a spacing member formed from poly methyl methacrylate ultrasonically welded to the implant.

5. A polymer composite implant consisting of a first layer of substantially ultra high molecular weight polyethylene and a second layer of a homogeneous blend of poly methyl methacrylate and polyethylene.

* * * * *